US009546916B1

(12) United States Patent
Crane et al.

(10) Patent No.: US 9,546,916 B1
(45) Date of Patent: Jan. 17, 2017

(54) DEVICES AND METHODS FOR MEASURING AND PROCESSING CONDITIONS OF CONTAINERS

(71) Applicant: Bottletech, LLC, San Francisco, CA (US)

(72) Inventors: Steven Peter Crane, Redwood City, CA (US); Robert James Zeches, San Francisco, CA (US)

(73) Assignee: BOTTLETECH, LLC, San Francisco, CA (US)

( * ) Notice: Subject to any disclaimer, the term of this patent is extended or adjusted under 35 U.S.C. 154(b) by 415 days.

(21) Appl. No.: 14/137,687

(22) Filed: Dec. 20, 2013

Related U.S. Application Data

(60) Provisional application No. 61/740,427, filed on Dec. 20, 2012.

(51) Int. Cl.
*G01K 13/00* (2006.01)
*G01N 25/56* (2006.01)
*B65D 79/02* (2006.01)

(52) U.S. Cl.
CPC .............. *G01K 13/00* (2013.01); *B65D 79/02* (2013.01); *G01N 25/56* (2013.01); *G01K 2207/04* (2013.01)

(58) Field of Classification Search
CPC ............ G01K 2207/04; B35D 23/006–23/008; B65D 23/16; B65D 79/02
USPC ........................................................ 374/150
See application file for complete search history.

(56) References Cited

U.S. PATENT DOCUMENTS

| 8,094,014 B2* | 1/2012 | Ransch | B65D 51/248 340/540 |
| 8,638,439 B2* | 1/2014 | Svanberg | G01N 21/1702 356/437 |
| 2006/0026971 A1* | 2/2006 | Sharpe | G01J 5/0037 62/126 |
| 2006/0202042 A1* | 9/2006 | Chu | G06K 17/0022 235/492 |
| 2008/0218348 A1* | 9/2008 | August | G06K 19/0717 340/572.1 |

FOREIGN PATENT DOCUMENTS

| JP | 2010100420 A | * | 5/2010 | |
| RU | 2135993 C1 | * | 8/1999 | |
| WO | WO 0233404 A2 | * | 4/2002 | ........... G01N 33/146 |

* cited by examiner

*Primary Examiner* — Minh Phan
*Assistant Examiner* — Leon W Rhodes, Jr.
(74) *Attorney, Agent, or Firm* — Jones Day

(57) ABSTRACT

Device and Method for measuring and processing one or more conditions of a container. The device includes one or more microcontrollers, one or more temperature sensors, and one or more humidity sensors. The one or more temperature sensors are configured to measure one or more temperatures of a container, inside the container, or outside the container, generate one or more temperature signals associated with one or more temperature data representing the measured one or more temperatures, and output the one or more temperature signals to the one or more microcontrollers. The one or more humidity sensors are configured to measure one or more humidity levels outside the container, generate one or more humidity signals associated with one or more humidity data representing the measured one or more humidity levels, and output the one or more humidity signals to the one or more microcontrollers.

10 Claims, 9 Drawing Sheets

DEVICES AND METHODS FOR MEASURING AND PROCESSING CONDITIONS OF CONTAINERS

1. CROSS-REFERENCES TO RELATED APPLICATIONS

This application claims priority to U.S. Provisional Application No. 61/740,427, filed Dec. 20, 2012, incorporated by reference herein for all purposes.

2. BACKGROUND OF THE INVENTION

The present invention is directed to measuring and/or processing devices and methods. More particularly, the invention provides devices and methods for measuring and processing conditions of containers. Merely by way of example, the invention has been applied to measuring and processing ambient temperature, ambient relative humidity, location, and/or acceleration of bottles that contain liquids, and/or the temperature and/or chemical composition of the contents. However, it would be recognized that the invention has a much broader range of applicability.

In the wine industry, certain conventional technology provides ways to measure instantaneous temperatures of individual bottles and/or containers through various technologies (e.g., contact-less infrared technology, contact thermocouple technology) to enable users to consume contents (e.g., wines) of the bottles and/or containers at particular temperatures. Other conventional technologies also provide comparison between measured instantaneous temperatures and desired consumption temperatures for particular contents (e.g., 64° F. for Bordeaux), using display technologies that are pleasing to the users. Additionally, conventional technology already exists to measure and maintain temperatures and relative humidity levels of separate storage areas, each of which is large enough to house multiple bottles for the purpose of ensuring consistent environmental conditions until the bottles are removed to be transported or the contents consumed.

Hence, it is highly desirable to improve techniques for measuring and processing ambient conditions of individual containers.

3. BRIEF SUMMARY OF THE INVENTION

The present invention is directed to measuring and/or processing devices and methods. More particularly, the invention provides devices and methods for measuring and processing conditions of containers. Merely by way of example, the invention has been applied to measuring and processing ambient temperature, ambient relative humidity, location, and/or acceleration of bottles that contain liquids, and/or the temperature and/or chemical composition of the contents. However, it would be recognized that the invention has a much broader range of applicability.

According to one embodiment, a device for measuring and processing one or more conditions of a container includes one or more microcontrollers, one or more temperature sensors, and one or more humidity sensors. The one or more temperature sensors are configured to measure one or more temperatures of a container, inside the container, or outside the container, generate one or more temperature signals associated with one or more temperature data representing the measured one or more temperatures, and output the one or more temperature signals to the one or more microcontrollers. The one or more humidity sensors are configured to measure one or more humidity levels outside the container, generate one or more humidity signals associated with one or more humidity data representing the measured one or more humidity levels, and output the one or more humidity signals to the one or more microcontrollers. Additionally, the device includes one or more memories coupled to the one or more microcontrollers, and a housing configured to enclose at least the one or more microcontrollers and the one or more memories. The one or more microcontrollers are configured to receive the one or more temperature signals and the one or more humidity signals, process information associated with the one or more temperature signals and the one or more humidity signals, and store the one or more temperature data and the one or more humidity data to the one or more memories coupled to the one or more microcontrollers. The housing is tamper resistant and configured to prevent one or more users from altering the one or more temperature data and the one or more humidity data.

According to another embodiment, a device for measuring and processing one or more conditions of a container includes one or more microcontrollers, one or more temperature sensors, and one or more humidity sensors. The one or more temperature sensors are configured to measure one or more temperatures of a container, inside the container, or outside the container, generate one or more temperature signals associated with one or more temperature data representing the measured one or more temperatures, and output the one or more temperature signals to the one or more microcontrollers. The one or more humidity sensors are configured to measure one or more humidity levels outside the container, generate one or more humidity signals associated with one or more humidity data representing the measured one or more humidity levels, and output the one or more humidity signals to the one or more microcontrollers. Additionally, the device includes one or more memories coupled to the one or more microcontrollers, a housing configured to enclose at least the one or more microcontrollers and the one or more memories, and one or more displays coupled to the one or more microcontrollers. The one or more microcontrollers are configured to receive the one or more temperature signals and the one or more humidity signals, process information associated with the one or more temperature signals and the one or more humidity signals, determine one or more additional data based on at least information associated with the one or more temperature data or the one or more humidity data, and store the one or more temperature data, the one or more humidity data, and the determined one or more additional data to the one or more memories. The one or more displays are configured to display at least some of the determined one or more additional data stored in the one or more memories, and the housing is tamper resistant and configured to prevent one or more users from altering the one or more additional data.

According to yet another embodiment, a device for measuring and processing one or more conditions of a container includes one or more microcontrollers, one or more optodes, and one or more timing devices. The one or more optodes are configured to measure one or more concentrations of one or more materials within a gaseous content or a liquid content of a container, generate one or more concentration signals associated with one or more concentration data representing the measured one or more concentrations, and output the one or more concentration signals to the one or more microcontrollers. The one or more timing devices are coupled to the one or more microcontrollers and configured to provide one or more date and time data for the one or more concentration data. Additionally, the device includes one or more memories coupled to the one or more microcontrollers, and a housing configured to enclose at least the one or more microcontrollers and the one or more memories. The one or more microcontrollers are configured to receive the one or more concentration data and the one or more date and time data, process information associated with the one or more concentration data and the one or more date and time data, match the one or more date and time data with the one or more concentration data respectively, and store the one or more concentration data and the one or more date and time data to the one or more memories.

According to yet another embodiment, a method for measuring and processing one or more conditions of a container includes measuring one or more temperatures of a container, insider the container, or outside the container, generating one or more temperature signals associated with one or more temperature data representing the measured one or more temperatures, outputting the one or more temperature signals, measuring one or more humidity levels outside the container, generating one or more humidity signals associated with one or more humidity data representing the measured one or more humidity levels, and outputting the one or more humidity signals. Additionally, the method includes receiving the one or more temperature signals and the one or more humidity signals, processing information associated with the one or more temperature signals and the one or more humidity signals, storing the one or more temperature data and the one or more humidity data, and preventing one or more users from altering the one or more temperature data and the one or more humidity data.

According to yet another embodiment, a method for measuring and processing one or more conditions of a container includes measuring one or more temperatures of a container, insider the container, or outside the container, generating one or more temperature signals associated with one or more temperature data representing the measured one or more temperatures, outputting the one or more temperature signals, measuring one or more humidity levels outside the container, generating one or more humidity signals associated with one or more humidity data representing the measured one or more humidity levels, and outputting the one or more humidity signals to the one or more microcontrollers. Additionally, the method includes receiving the one or more temperature signals and the one or more humidity signals, processing information associated with the one or more temperature signals and the one or more humidity signals, determining one or more additional data based on at least information associated with the one or more temperature data or the one or more humidity data, storing the one or more temperature data, the one or more humidity data, and the determined one or more additional data, displaying at least some of the determined one or more additional data stored in the one or more memories, and preventing one or more users from altering the one or more additional data.

According to yet another embodiment, a method for measuring and processing one or more conditions of a container includes measuring one or more concentrations of one or more materials within a gaseous content or a liquid content of a container, generating one or more concentration signals associated with one or more concentration data representing the measured one or more concentrations, outputting the one or more concentration signals, providing one or more date and time data for the one or more concentration data, receiving the one or more concentration data and the one or more date and time data, processing information associated with the one or more concentration data and the one or more date and time data, matching the one or more date and time data with the one or more concentration data respectively, and storing the one or more concentration data and the one or more date and time data to the one or more memories.

Depending upon the embodiment, one or more benefits may be achieved. These benefits and various additional objects, features, and advantages of the present invention can be fully appreciated with reference to the detailed description and accompanying drawings that follow.

4. BRIEF DESCRIPTION OF THE DRAWINGS

5. DETAILED DESCRIPTION OF THE INVENTION

The present invention is directed to measuring and/or processing devices and methods. More particularly, the invention provides devices and methods for measuring and processing conditions of containers. Merely by way of example, the invention has been applied to measuring and processing ambient temperature, ambient relative humidity, location, and/or acceleration of bottles that contain liquids, and/or the temperature and/or chemical composition of the contents. However, it would be recognized that the invention has a much broader range of applicability.

Figure 1:
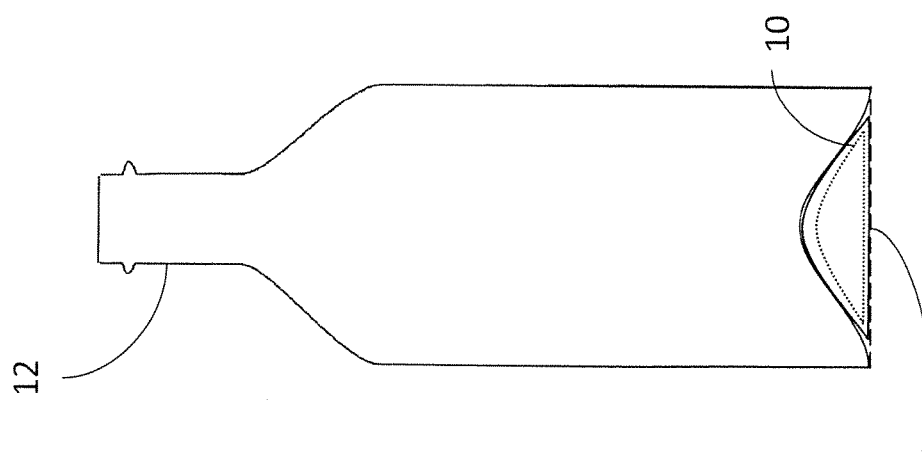
FIG. 1 is a simplified diagram showing a side view of a device for measuring and processing one or more conditions of a container according to one embodiment of the present invention.
Figure 2:
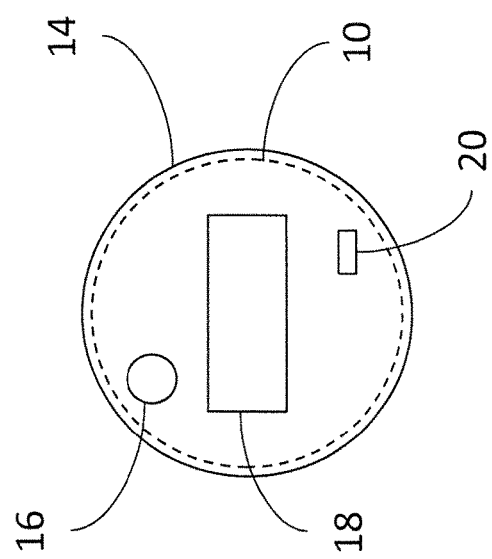
FIG. 2 is a simplified diagram showing a bottom view of the device for measuring and processing the one or more conditions of the container according to one embodiment of the present invention.

FIG. 1 is a simplified diagram showing a side view of a device for measuring and processing one or more conditions of a container according to one embodiment of the present invention, and FIG. 2 is a simplified diagram showing a bottom view of the device for measuring and processing the one or more conditions of the container according to one embodiment of the present invention. These diagrams are merely examples, which should not unduly limit the scope of the claims. One of ordinary skill in the art would recognize many variations, alternatives, and modifications.

As shown in FIGS. 1 and 2, the device 10 (e.g., a powered device) is configured to measure, record, and display one or more ambient conditions (e.g., ambient temperature and/or ambient relative humidity) of a container 12. For example, the container 12 is a liquid-containing bottle. In another example, the device 10 is enclosed in a housing 14 that is affixed to the bottom of the container 12 (e.g., the bottom of a liquid-containing bottle). In yet another example, the device 10 includes a user input component 16 (e.g., a button), a display 18, and a wired input/output component 20 (e.g., a connector). In yet another example, the user input component 16, the display 18, and the wired input/output component 20 are housed on the bottom of the device 10.

In one embodiment, the user input component 16 (e.g., the button) is configured to allow a user to change the state of the device 10. For example, the user, by pressing the button 16, changes the device 10 from the "display on" state to the "display off" state, or from the "display off" state to the "display on" state. In another example, under the "display on" state, the display 18 is turned on, and under the "display off" state, the display 18 is turned off (e.g., in order to save power when the user does not need to read the data). In yet another example, the user, by pressing the button 16 multiple times, cycles through a series of states of the device 10 that includes the "display off" state and one or more "display on" states. In yet another example, the one or more "display on" states include a state for displaying the historical temperature range; a state for displaying the highest measured temperature, its duration, and its date; a state for displaying the second highest measured temperature, its duration, and its date; a state for displaying the lowest temperature, its duration, and its date; a state for displaying the fastest rate of temperature change, its range, and its date; and/or a state for displaying the historical relative humidity range.

In another embodiment, the display 18 is configured to display to the user data that are stored in the device 10. For example, the display 18 is configured to display one or more measured temperatures of the ambient air that is close to but outside the container 12, one or more measured temperatures of the container 12, and/or one or more temperatures of the liquid that is inside the container 12. In another example, the one or more temperatures of the liquid is determined by the device 10 (e.g., by a microcontroller as part of the device 10) based on the one or more measured temperatures of the ambient air and/or the one or more measured temperatures of the container 12. In yet another example, the display 18 is configured to display one or more measured relative humidity data of the ambient air that is close to but outside the container 12.

In yet another embodiment, the wired input/output component 20 (e.g., the connector) is configured to allow a user to charge and/or recharge the device 10, and/or to transfer data from and/or to the device 10. For example, the data are transferred between the device 10 and a smartphone, or between the device 10 and a computer. In another example, the data are stored in the device 10 before the data are transferred out of the device 10 or after the data are transferred into the device 10. In yet another example, the connector 20 is a USB connection port or another type of wired connection port that allows electric charging and/or recharging and/or allows data transfer. In yet another example, the device 10 is configured to alert a user that electric charging or recharging is needed by providing warning sound, by providing wired and/or wireless electronic signal, and/or by providing visual display (e.g., on the display 18). In yet another embodiment, the housing 14 is tamper resistant so that the data stored in the device 10 cannot be improperly altered and/or the device 10 cannot be improperly replaced by another device that stores counterfeit data.

As discussed above and further emphasized here, FIGS. 1 and 2 are merely examples, which should not unduly limit the scope of the claims. One of ordinary skill in the art would recognize many variations, alternatives, and modifications. For example, the wired input/output component 20 (e.g., the connector) is removed. In one embodiment, the device 10 is configured to provide wireless data connection (e.g., by Bluetooth, Induction Wireless, WiFi, RFID, and/or cellular wireless connection), and/or provide wireless electric charging and recharging (e.g. by near-field RF). In another embodiment, the device 10 is configured to charge and recharge itself by harvesting energy from the ambient environment (e.g., from vibration and/or from stray EMF). In another example, the user input component 16 (e.g., the button) is removed. In one embodiment, the display 18 is a touch screen. In another embodiment, the user uses the touch screen (e.g., use a virtual button displayed on the display 18) to change the state of the device 10.

Figure 3:
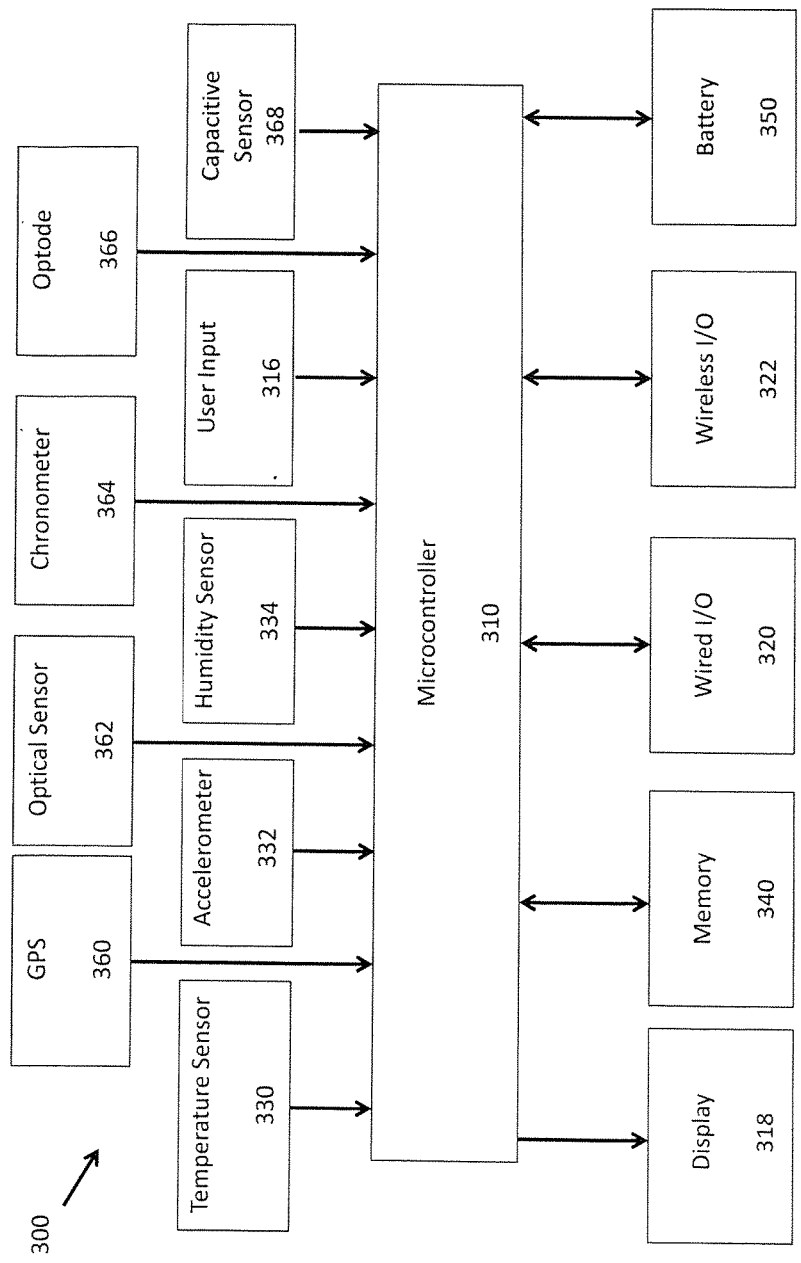
FIG. 3 is a simplified diagram showing certain components of a device for measuring and processing one or more conditions of a container according to one embodiment of the present invention.

FIG. 3 is a simplified diagram showing certain components of a device for measuring and processing one or more conditions of a container according to one embodiment of the present invention. This diagram is merely an example, which should not unduly limit the scope of the claims. One of ordinary skill in the art would recognize many variations, alternatives, and modifications. The device 300 includes a user input component 316 (e.g., a button), a display 318, a wired input/output component 320 (e.g., a connector), a wireless input/output component 322, a microcontroller 310, a temperature sensor 330, an accelerometer 332, a humidity sensor 334, a memory 340, a battery 350, a GPS component 360, an optical sensor 362, a chronometer 364, an optode 366, and a capacitive sensor 368. For example, the container is the container 12 as shown in FIGS. 1 and 2, the container 412 as shown in FIG. 4, the container 512 as shown in FIG. 5, the container 612 as shown in FIG. 6, the container 712 as shown in FIGS. 7 and 8, and/or the container 912 as shown in FIG. 9.

In one embodiment, the display 318 includes an LCD display, an OLED display, and/or a touch screen. In another embodiment, the humidity sensor 334 is a relative humidity sensor. In yet another embodiment, the memory 340 is a non-volatile memory that is configured to store data. In yet another embodiment, the battery 350 is a rechargeable battery that is configured to provide power to other components of the device 300. For example, the battery 350 is coupled to the microcontroller 310.

According to one embodiment, some or all of the user input component 316, the display 318, the wired input/output component 320, the wireless input/output component 322, the microcontroller 310, the temperature sensor 330, the accelerometer 332, the humidity sensor 334, the memory 340, the battery 350, the GPS component 360 (e.g., including a GPS signal receiver), the optical sensor 362, the chronometer 364, the optode 366, and the capacitive sensor 368 are enclosed, partially or entirely, in a housing (e.g., a tamper resistant housing) that is attached to the container (e.g., the container 12, the container 412, the container 512, the container 612, the container 712, and/or the container 912).

Figure 4:
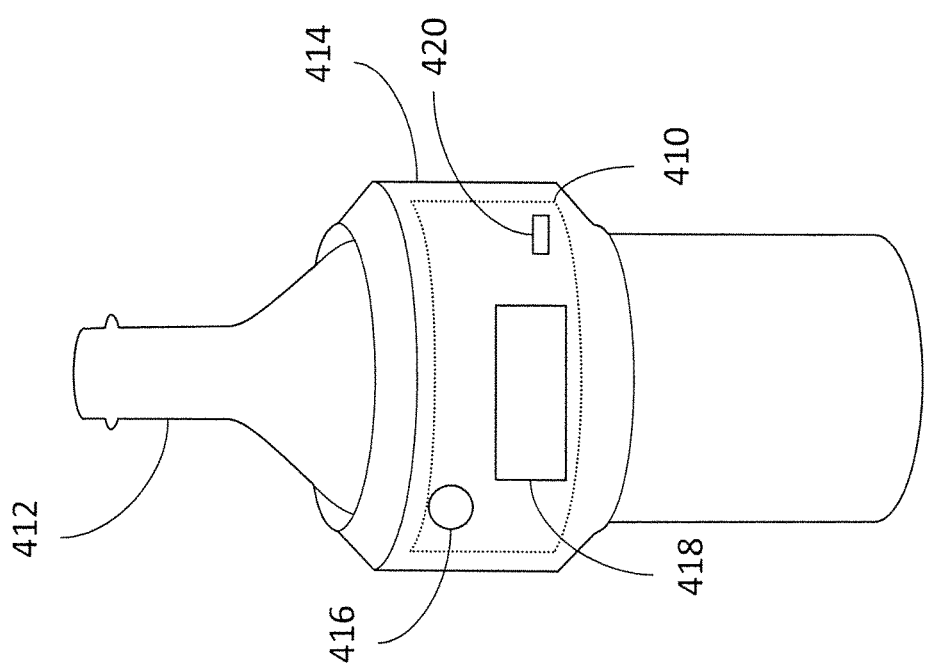
FIG. 4 is a simplified diagram showing a side view of a device for measuring and processing one or more conditions of a container according to another embodiment of the present invention.
Figure 5:
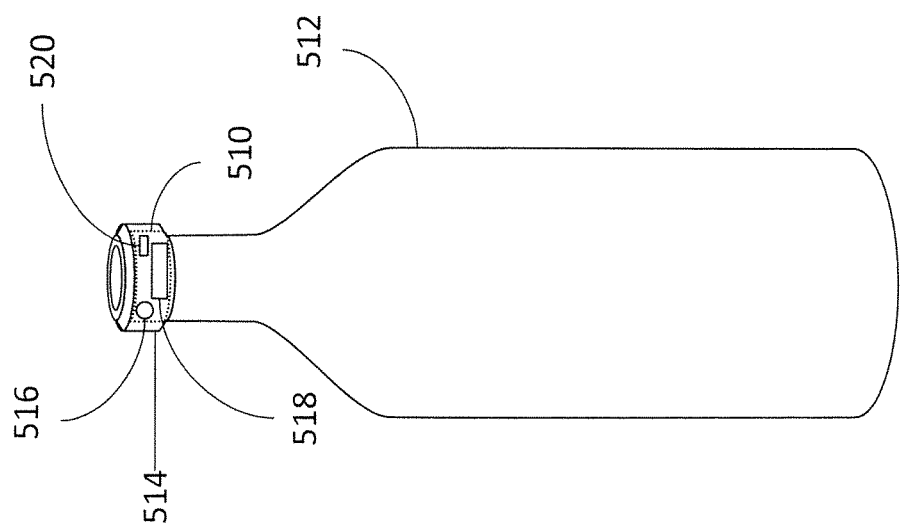
FIG. 5 is a simplified diagram showing a side view of a device for measuring and processing one or more conditions of a container according to another embodiment of the present invention.
Figure 6:
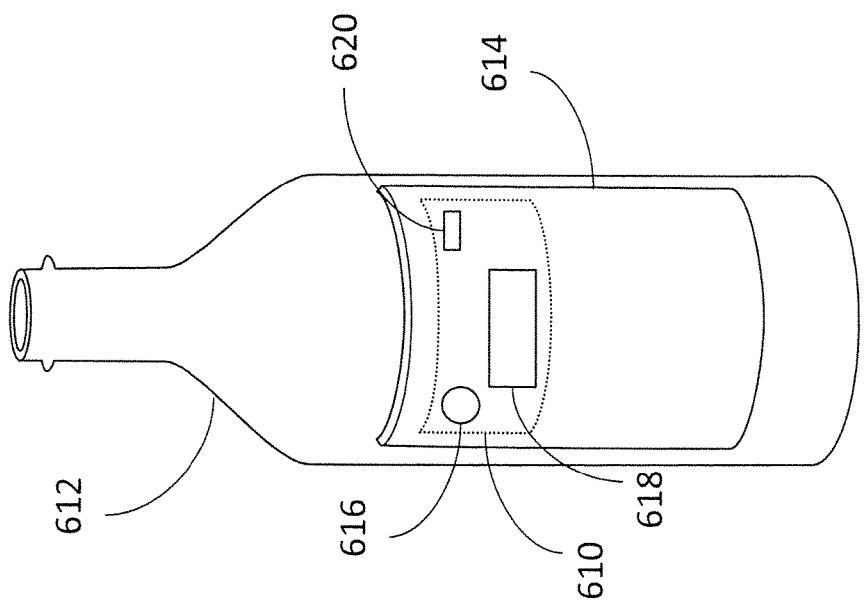
FIG. 6 is a simplified diagram showing a side view of a device for measuring and processing one or more conditions of a container according to another embodiment of the present invention.
Figure 7:
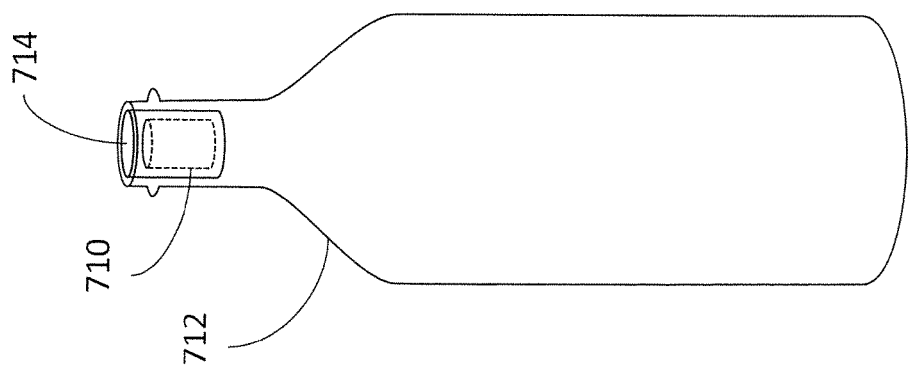
FIG. 7 is a simplified diagram showing a side view of a device for measuring and processing one or more conditions of a container according to one embodiment of the present invention.
Figure 8:
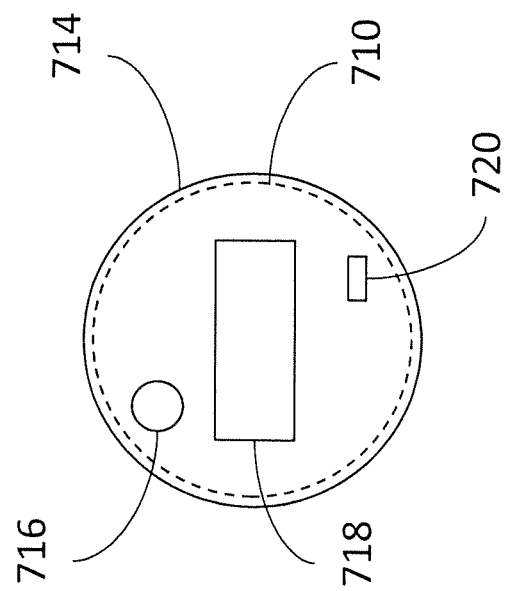
FIG. 8 is a simplified diagram showing a top view of the device for measuring and processing the one or more conditions of the container according to one embodiment of the present invention.
Figure 9:
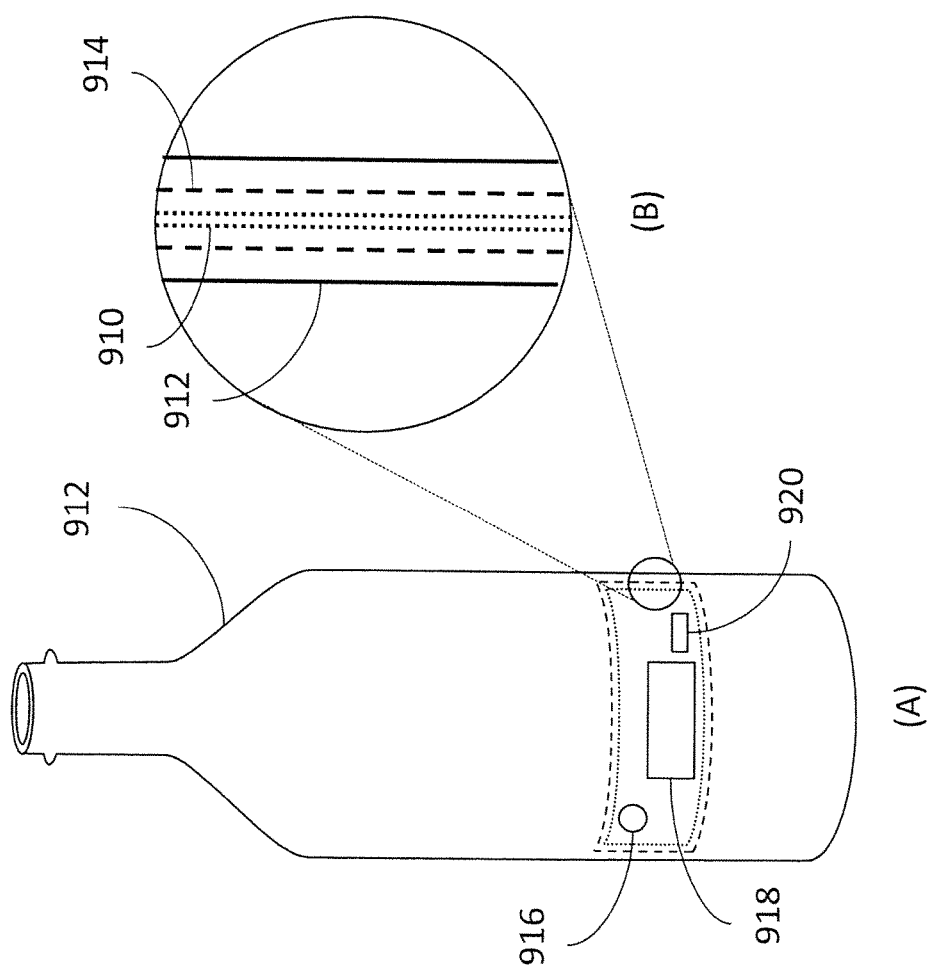
FIG. 9(A) is a simplified diagram showing a side view of a device for measuring and processing one or more conditions of a container according to one embodiment of the present invention.
FIG. 9(B) is a simplified diagram showing a cross-section view of part of the device for measuring and processing the one or more conditions of the container according to one embodiment of the present invention.

For example, the tamper resistant housing is the housing 14 as shown in FIGS. 1 and 2, the housing 414 as shown in FIG. 4, the housing 514 as shown in FIG. 5, the housing 614 as shown in FIG. 6, the housing 714 as shown in FIGS. 7 and 8, and/or the housing 914 as shown in FIG. 9. In another example, the tamper resistant housing prevents the data stored in the device 300 from being improperly altered and/or prevents the device 300 from being improperly replaced by another device that stores counterfeit data. In one embodiment, the tamper resistance is provided by one or more mechanical mechanisms, such as one or more tamper-indicating seals and/or one or more sacrificial housing components. In another embodiment, the tamper resistance is provided by one or more electronic mechanisms. For example, the memory 340 includes a read-only memory component and a read-write memory component. In another example, certain data (e.g., the wine producer, the label details, the vintage, the varietal, the vineyard location with GPS coordinates, the bottling location with GPS coordinates, and/or generic "source location") are pre-stored in the read-only memory component, but other data are written to the read-write memory component that allows the users limited control over sampling time and/or conditions over limited time spans. In yet another example, the measured data (e.g., the measured data from the temperature sensor 330, the accelerometer 332, the humidity sensor 334, the GPS component 360, the optical sensor 362, the optode 366, and/or the capacitive sensor 368) cannot be altered after such data are written into the read-write memory by the microcontroller 310.

For example, the device 300 is the same as the device 10. In another example, the user input component 316 is the same as the user input component 16, the display 318 is the same as the display 18, and the wired input/output component 320 is the same as the wired input/output component 20.

According to another embodiment, the microcontroller 310 is coupled to some or all of the user input component 316, the display 318, the wired input/output component 320, the wireless input/output component 322, the microcontroller 310, the temperature sensor 330, the accelerometer 332, the humidity sensor 334, the memory 340, the battery 350, the GPS component 360, the optical sensor 362, the chronometer 364, the optode 366, and the capacitive sensor 368. For example, the microcontroller 310 is configured to receive one or more signals from one or more other components (e.g., the temperature sensor 330, the accelerometer 332, the humidity sensor 334, the GPS component 360, the optical sensor 362, the optode 366, and/or the capacitive sensor 368), process information associated with the received one or more signals, store to the memory 340 one or more measured data represented by the received one or more signals. In another example, the microcontroller 310 is configured to receive one or more signals from one or more other components (e.g., the temperature sensor 330, the accelerometer 332, the humidity sensor 334, the GPS component 360, the optical sensor 362, the optode 366, and/or the capacitive sensor 368), process information associated with the received one or more signals, determine one or more derived data based on one or more measured data that are represented by the received one or more signals, store to the memory 340 the one or more measured data and/or the one or more derived data.

In one embodiment, the one or more signals and/or the one or more represented data from one or more sensors (e.g., the temperature sensor 330, the accelerometer 332, the humidity sensor 334, the GPS component 360, the optical sensor 362, the optode 366, and/or the capacitive sensor 368) are used to provide an overall assessment of the quality of the content of the container (e.g., the wine inside a bottle). For example, the overall assessment of the quality includes the overall historical conditions of the container that could affect such quality. In another example, one or more thermal profiles are analyzed in aggregate to gauge the efficacy of a pharmaceutical insider the container by using baseline data supplied by the manufacturer, in order to provide improved safety to the consumers and/or provide more accurate expiration information. In yet another example, one or more thermal profiles and one or more data from the optode 366 are analyzed in aggregate to gauge the safety of perishable goods for consumption, providing improved safety to the consumers. In yet another example, the one or more data from the optode 366 represent presence or absence and/or one or more concentrations of one or more volatile compounds associated with food spoilage insider the container.

In another embodiment, the one or more signals and/or the one or more represented data (e.g., location data, acceleration data, capacitance data, and optical data) are analyzed in aggregate to determine content authenticity and/or signs of tampering of the container. For example, the location information is compared against standard supply-chain routes and combined with acceleration and capacitance data to determine if the content of the container was re-routed to an unapproved site and/or removed from the container. In yet another embodiment, the one or more signals and/or represented data (e.g., thermal profiles, acceleration data, relative humidity data, and optode data) are analyzed in aggregate to determine the overall quality of wine as a function of storage conditions over time after bottling. For example, the one or more signals and/or represented data are further analyzed to indicate to the user an overall assessment or score and/or a specific timeframe for which the content of the container is best consumed.

In yet another embodiment, the temperature sensor 330 is configured to measure temperature of the ambient air that is close to but outside the container (e.g., the container 12, the container 412, the container 512, the container 612, the container 712, and/or the container 912), measure temperature inside the container (e.g., the container 12, the container 412, the container 512, the container 612, the container 712, and/or the container 912), and/or measure temperature of the container (e.g., the container 12, the container 412, the container 512, the container 612, the container 712, and/or the container 912). For example, the temperature inside the container is the temperature of a content (e.g., a liquid content) of the container. In another example, the temperature inside the container is the temperature of the wine inside the container. In yet another example, the temperature sensor 330 is an optical temperature sensor (e.g., an infrared temperature sensor). In yet another example, the temperature sensor 330 is a thermocouple temperature sensor.

In yet another embodiment, the accelerometer 332 is configured to detect the acceleration of the container (e.g., the container 12, the container 412, the container 512, the container 612, the container 712, and/or the container 912). In yet another embodiment, the humidity sensor 334 is configured to measure relative humidity of the ambient air that is close to but outside the container (e.g., the container 12, the container 412, the container 512, the container 612, the container 712, and/or the container 912). For example, the humidity sensor 334 is exposed to the ambient air.

According to one embodiment, the user input component 316 (e.g., a button) is configured to allow a user to change the state of the device 300. For example, the user, by pressing the button 316, changes the device 300 from the "display on" state to the "display off" state, or from the "display off" state to the "display on" state. In another example, the user, by pressing the button 316 multiple times, cycles through a series of states of the device 300 that includes the "display off" state and one or more "display on" states. In yet another example, the one or more "display on" states include displaying one or more temperatures in different units (e.g. F, K, C). In yet another example, the one or more "display on" states include displaying the GPS data (e.g., the position data) in different formats (e.g., WGS84, UTM). In yet another example, the one or more "display on" status include displaying data with or without using one or more proximity and ambient light sensors.

According to another embodiment, the display 318 is configured to display to the user data that are stored in the device 300 (e.g., data that are stored in the memory 340). For example, the data stored in the memory 340 are one or more measured temperatures of the ambient air that is close to but outside the container, one or more measured temperatures of the container, one or more temperatures of the liquid that is inside the container, and/or one or more data representing one or more rates of changes for one or more temperatures. In another example, the one or more temperatures of the liquid inside the container are derived by the microcontroller 310 from the one or more measured temperatures of the container. In yet another example, the one or more data representing one or more rates of changes for one or more temperatures are derived by the microcontroller 310 from the one or more temperatures.

According to yet another embodiment, the wired input/output component 320 (e.g., the connector) is configured to allow a user to charge and/or recharge the device 300 (e.g., charge and/or recharge the battery 350 using an external power source), and/or to transfer data from and/or to the device 10 (e.g., transfer data from and/or to the memory 340). For example, the connector 320 is a USB connection port or another type of wired connection port that allows electric charging and/or recharging and/or allows data transfer. According to yet another embodiment, the wireless input/output component 322 (e.g., including a wireless transceiver) is configured to provide wireless data connection (e.g., by Bluetooth, Induction Wireless, WiFi, RFID, and/or cellular wireless connection), and/or provide wireless electric charging and recharging (e.g. charging and/or recharging the battery 350 by near-field RF using an external power source). For example, the data are transferred wirelessly between the device 300 and a smartphone, or between the device 300 and a computer.

In one embodiment, the GPS component 360 is configured to detect the GPS signal. For example, the detected GPS signal is sent to the microcontroller 310, which uses the GPS signal to determine position of the container (e.g., the container 12, the container 412, the container 512, the container 612, the container 712, and/or the container 912). In another embodiment, the optical sensor 362 is configured to detect an optical signal in order to determine whether the container (e.g., the container 12, the container 412, the container 512, the container 612, the container 712, and/or the container 912) was emptied at any point in time.

In yet another embodiment, the chronometer 364 is configured to measure time accurately. For example, the chronometer 364 is configured and referenced using the clock signal received by the GPS component 360 in order to maintain accurate time records over long measuring cycles. In another example, the chronometer 364 is configured to provide one or more date and time data for the one or more data, that are measured by or derived from one or more measurements performed by the temperature sensor 330, the accelerometer 332, the humidity sensor 334, the GPS component 360, the optical sensor 362, the optode 366, and/or the capacitive sensor 368. In yet another example, the microcontroller 310 is configured to match the one or more date and time data with the one or more data that are measured or derived from the one or more measurements. In yet another example, the display 318 is configured to display the one or more data that are measured or derived from the one or more measurements and also display the matched one or more date and time data.

In yet another embodiment, the optode 366 is configured to measure the presence and/or the concentration of each of one or more materials within the liquid content of the container (e.g., the translucent container). For example, the translucent container is the container 12, the container 412, the container 512, the container 612, the container 712, and/or the container 912. In another example, the container is a glass bottle, and the liquid content is wine. In yet another example, the optode 366 is an oxygen optode, which is configured to measure the dissolved oxygen concentration within the liquid content (e.g., wine) of the container (e.g., the translucent container) over time, and/or measure the oxygen concentration within the gaseous content (e.g., air) of the container (e.g., the translucent container) over time. In yet another example, the container contains both the liquid content (e.g., wine) and the gaseous content (e.g., air between wine and cork). In yet another example, the optode 366 is an amines optode, which is configured to measure the dissolved amine concentration within the liquid content (e.g., wine) of the container (e.g., the translucent container) over time. In yet another example, the optode 366 includes multiple optodes (e.g., an oxygen optode and an amines optode).

In yet another embodiment, the capacitive sensor 368 is configured to determine presence or absence of one or more materials (e.g., a liquid) inside the container (e.g., the container 12, the container 412, the container 512, the container 612, the container 712, and/or the container 912). For example, the capacitive sensor 368 is configured to determine whether the container was emptied at any point in time.

As discussed above and further emphasized here, FIG. 3 is merely an example, which should not unduly limit the scope of the claims. One of ordinary skill in the art would recognize many variations, alternatives, and modifications. In one embodiment, the housing (e.g., the housing 14 as shown in FIGS. 1 and 2, the housing 414 as shown in FIG. 4, the housing 514 as shown in FIG. 5, the housing 614 as shown in FIG. 6, the housing 714 as shown in FIGS. 7 and 8, and/or the housing 914 as shown in FIG. 9) is not tamper resistant. In another embodiment, the user input component 316 is removed, and the display 318 is a touch screen. In yet another embodiment, the wired input/output component 320 is removed, but the wireless input/output component 322 is kept. In yet another embodiment, the accelerometer 332, the GPS component 360, and/or the optical sensor 362 is removed. In yet another embodiment, the chronometer 364 is removed or replaced by another device that measures date and time.

In yet another embodiment, an analog-to-digital converter is added and configured to convert analog output signals of certain components to digital signals that are then received by the microcontroller 310. For example, these certain components include the user input component 316, the temperature sensor 330, the accelerometer 332, the humidity sensor 334, the GPS component 360, the optical sensor 362, the chronometer 364, and/or the oxygen optode 366. In yet another embodiment, the optode 366 is replaced by another type of sensor (e.g., a contact-less sensor) for analyzing the content of the container over time. For example, the contact-less sensor includes an optical sensor. In yet another embodiment, the optode 366 is removed from the device 300, which still includes the optical sensor 362. In yet another embodiment, the optical sensor 362 is removed from the device 300, which still includes the capacitive sensor 368. In yet another embodiment, the capacitive sensor 368 is removed from the device 300, which still includes the optical sensor 362.

According to one embodiment, the device 300 is a microcontroller-driven sensor array apparatus. For example, the microcontroller-driven sensor array apparatus is configured to measure the ambient temperature surrounding the apparatus, measure the relative humidity surrounding the apparatus, and/or measure the accelerating forces surrounding the apparatus in three axes. In another example, the sensor array includes the temperature sensor 330, the accelerometer 332, the humidity sensor 334, the GPS component 360, and/or the optical sensor 362. In yet another example, the microcontroller-driven sensor array apparatus is further configured to record the values output from the sensor array, and/or mark the time of the recording using a real-time clock apparatus (e.g., the chronometer 364). According to another embodiment, the device 300 (e.g., the microcontroller-driven sensor array apparatus) includes an sensing surface configured to be exposed to the ambient relative humidity, and the humidity sensor 334 that is located below the sensing surface and configured to detect the humidity of the sensing surface and to output a signal representing the measured humidity to the microcontroller 310. For example, the microcontroller 310 is configured to process and evaluate the signal received from the humidity sensor 334.

According to yet another embodiment, the device 300 (e.g., the microcontroller-driven sensor array apparatus) includes the accelerometer 332 that is configured to detect changes in accelerating forces in three axes and to output a signal representing the measured changes in acceleration to the microcontroller 310. For example, the microcontroller 310 is configured to process and evaluate the signal received from the accelerometer 332. According to yet another embodiment, the device 300 (e.g., the microcontroller-driven sensor array apparatus) includes the GPS component 360 that is configured to detect the GPS signal and to output a signal representing the measured position to the microcontroller 310. For example, the microcontroller 310 is configured to process and evaluate the signal received from the GPS component 360.

According to yet another embodiment, the device 300 (e.g., the microcontroller-driven sensor array apparatus) includes a data-recording component configured to digitally record the measured data and/or the derived data to the memory 340, from which the stored data can be retrieved. For example, the data-recording component includes the microcontroller 310 and the chronometer 364. In another example, the chronometer 364 is powered by a battery that is different from the battery 350, so that the chronometer 364 does not reset even if the battery 350 is removed or runs out of power. In yet another example, the data-recording component is configured to, when the recording is performed, mark the recording with the current value of the real-time clock (e.g., the current date and time of the chronometer 364). In yet another example, the microcontroller 310 is configured to, when the recorded data are retrieved from the memory 340, read the stored data from the memory and provide the corresponding date and time for the retrieved data. According to yet another embodiment, the battery 350 is a rechargeable battery that is portable and can be replaced by another battery. According to yet another embodiment, the user can set a time interval for collecting and recording data from the sensors (e.g., the temperature sensor 330, the accelerometer 332, the humidity sensor 334, the GPS component 360, and/or the optical sensor 362).

FIG. 4 is a simplified diagram showing a side view of a device for measuring and processing one or more conditions of a container according to another embodiment of the present invention. This diagram is merely an example, which should not unduly limit the scope of the claims. One of ordinary skill in the art would recognize many variations, alternatives, and modifications.

As shown in FIG. 4, the device 410 (e.g., a powered device) is configured to measure, record, and display one or more ambient conditions (e.g., ambient temperature and/or ambient relative humidity) of the container 412. For example, the container 412 is a liquid-containing bottle. In another example, the device 410 is enclosed in a housing 414 that is affixed around the exterior of the container 412 (e.g., around the exterior of a liquid-containing bottle). In yet another example, the device 410 includes a user input component 416 (e.g., a button), a display 418, and a wired input/output component 420 (e.g., a connector). In yet another example, the user input component 416, the display 418, and the wired input/output component 420 are housed on the side of the device 410. In yet another example, the device 410 is the same as the device 300. In yet another example, the user input component 416 is the same as the user input component 316, the display 418 is the same as the display 318, and the wired input/output component 420 is the same as the wired input/output component 320.

In one embodiment, the user input component 416 (e.g., the button) is configured to allow a user to change the state of the device 410. For example, the user, by pressing the button 416, changes the device 410 from the "display on" state to the "display off" state, or from the "display off" state to the "display on" state. In another example, under the "display on" state, the display 418 is turned on, and under the "display off" state, the display 418 is turned off (e.g., in order to save power when the user does not need to read the data). In yet another example, the user, by pressing the button 416 multiple times, cycles through a series of states of the device 410 that includes the "display off" state and one or more "display on" states. In yet another example, the one or more "display on" states include a state for displaying the historical temperature range, a state for displaying the highest measured temperature, its duration, and its date, a state for displaying the second highest measured temperature, its duration, and its date, a state for displaying the lowest temperature, its duration, and its date, and/or a state for displaying the historical relative humidity range.

In another embodiment, the display 418 is configured to display to the user data that are stored in the device 410. For example, the display 418 is configured to display one or more measured temperatures of the ambient air that is close to but outside the container 412, one or more measured temperatures of the container 412, and/or one or more temperatures of the liquid that is inside the container 412. In another example, the one or more temperatures of the liquid is determined by the device 410 (e.g., by a microcontroller as part of the device 410) based on the one or more measured temperatures of the ambient air and/or the one or more measured temperatures of the container 412. In yet another example, the display 418 is configured to display one or more measured relative humidity data of the ambient air that is close to but outside the container 412.

In yet another embodiment, the wired input/output component 420 (e.g., the connector) is configured to allow a user to charge and/or recharge the device 410, and/or to transfer data from and/or to the device 410. For example, the data are transferred between the device 410 and a smartphone, or between the device 410 and a computer. In another example, the data are stored in the device 410 before the data are transferred out of the device 410 or after the data are transferred into the device 410. In yet another example, the connector 420 is a USB connection port or another type of wired connection port that allows electric charging and/or recharging and/or allows data transfer. In yet another example, the device 410 is configured to alert a user that electric charging or recharging is needed by providing warning sound, by providing wired and/or wireless electronic signal, and/or by providing visual display (e.g., on the display 418). In yet another embodiment, the housing 414 is tamper resistant so that the data stored in the device 410 cannot be improperly altered and/or the device 410 cannot be improperly replaced by another device that stores counterfeit data.

As discussed above and further emphasized here, FIG. 4 is merely an example, which should not unduly limit the scope of the claims. One of ordinary skill in the art would recognize many variations, alternatives, and modifications. For example, the wired input/output component 420 (e.g., the connector) is removed. In one embodiment, the device 410 is configured to provide wireless data connection (e.g., by Bluetooth, Induction Wireless, WiFi, RFID, and/or cellular wireless connection), and/or provide wireless electric charging and recharging (e.g. by near-field RF). In another embodiment, the device 410 is configured to charge and recharge itself by harvesting energy from the ambient environment (e.g., from vibration and/or from stray EMF). In another example, the user input component 416 (e.g., the button) is removed. In one embodiment, the display 418 is a touch screen. In another embodiment, the user uses the touch screen (e.g., use a virtual button displayed on the display 418) to change the state of the device 410.

FIG. 5 is a simplified diagram showing a side view of a device for measuring and processing one or more conditions of a container according to another embodiment of the present invention. This diagram is merely an example, which should not unduly limit the scope of the claims. One of ordinary skill in the art would recognize many variations, alternatives, and modifications.

As shown in FIG. 5, the device 510 (e.g., a powered device) is configured to measure, record, and display one or more ambient conditions (e.g., ambient temperature and/or ambient relative humidity) of the container 512. For example, the container 512 is a liquid-containing bottle. In another example, the device 510 is enclosed in a housing 514 that is affixed around the neck of the container 512 (e.g., around the neck of a liquid-containing bottle). In yet another example, the device 510 includes a user input component 516 (e.g., a button), a display 518, and a wired input/output component 520 (e.g., a connector). In yet another example, the user input component 516, the display 518, and the wired input/output component 520 are housed on the side of the device 510. In yet another example, the device 510 is the same as the device 300. In yet another example, the user input component 516 is the same as the user input component 316, the display 518 is the same as the display 318, and the wired input/output component 520 is the same as the wired input/output component 320.

In one embodiment, the user input component 516 (e.g., the button) is configured to allow a user to change the state of the device 510. For example, the user, by pressing the button 516, changes the device 510 from the "display on" state to the "display off" state, or from the "display off" state to the "display on" state. In another example, under the "display on" state, the display 518 is turned on, and under the "display off" state, the display 518 is turned off (e.g., in order to save power when the user does not need to read the data). In yet another example, the user, by pressing the button 516 multiple times, cycles through a series of states of the device 510 that includes the "display off" state and one or more "display on" states. In yet another example, the one or more "display on" states include a state for displaying the historical temperature range, a state for displaying the highest measured temperature, its duration, and its date, a state for displaying the second highest measured temperature, its duration, and its date, a state for displaying the lowest temperature, its duration, and its date, and/or a state for displaying the historical relative humidity range.

In another embodiment, the display 518 is configured to display to the user data that are stored in the device 510. For example, the display 518 is configured to display one or more measured temperatures of the ambient air that is close to but outside the container 512, one or more measured temperatures of the container 512, and/or one or more temperatures of the liquid that is inside the container 512. In another example, the one or more temperatures of the liquid is determined by the device 510 (e.g., by a microcontroller as part of the device 510) based on the one or more measured temperatures of the ambient air and/or the one or more measured temperatures of the container 512. In yet another example, the display 518 is configured to display one or more measured relative humidity data of the ambient air that is close to but outside the container 512. In yet another example, the display 518 is configured to display the moisture content of a cork of the container 512 (e.g., a cork of a wine bottle), where the moisture content is measured by the device 510.

In yet another embodiment, the wired input/output component 520 (e.g., the connector) is configured to allow a user to charge and/or recharge the device 510, and/or to transfer data from and/or to the device 510. For example, the data are transferred between the device 510 and a smartphone, or between the device 510 and a computer. In another example, the data are stored in the device 510 before the data are transferred out of the device 510 or after the data are transferred into the device 510. In yet another example, the connector 520 is a USB connection port or another type of wired connection port that allows electric charging and/or recharging and/or allows data transfer. In yet another example, the device 510 is configured to alert a user that electric charging or recharging is needed by providing warning sound, by providing wired and/or wireless electronic signal, and/or by providing visual display (e.g., on the display 518). In yet another embodiment, the housing 514 is tamper resistant so that the data stored in the device 510 cannot be improperly altered and/or the device 510 cannot be improperly replaced by another device that stores counterfeit data.

As discussed above and further emphasized here, FIG. 5 is merely an example, which should not unduly limit the scope of the claims. One of ordinary skill in the art would recognize many variations, alternatives, and modifications. For example, the wired input/output component 520 (e.g., the connector) is removed. In one embodiment, the device 510 is configured to provide wireless data connection (e.g., by Bluetooth, Induction Wireless, WiFi, RFID, and/or cellular wireless connection), and/or provide wireless electric charging and recharging (e.g. by near-field RF). In another embodiment, the device 510 is configured to charge and recharge itself by harvesting energy from the ambient environment (e.g., from vibration and/or from stray EMF). In another example, the user input component 516 (e.g., the button) is removed. In one embodiment, the display 518 is a touch screen. In another embodiment, the user uses the touch screen (e.g., use a virtual button displayed on the display 518) to change the state of the device 510.

FIG. 6 is a simplified diagram showing a side view of a device for measuring and processing one or more conditions of a container according to another embodiment of the present invention. This diagram is merely an example, which should not unduly limit the scope of the claims. One of ordinary skill in the art would recognize many variations, alternatives, and modifications.

As shown in FIG. 6, the device 610 (e.g., a powered device) is configured to measure, record, and display one or more ambient conditions (e.g., ambient temperature and/or ambient relative humidity) of the container 612. For example, the container 612 is a liquid-containing bottle. In another example, the device 610 is enclosed in a housing 614 that is affixed to the side of the container 612 (e.g., to the side of a liquid-containing bottle). In yet another example, the device 610 includes a user input component 616 (e.g., a button), a display 618, and a wired input/output component 620 (e.g., a connector). In yet another example, the user input component 616, the display 618, and the wired input/output component 620 are housed on the side of the device 610. In yet another example, the device 610 is the same as the device 300. In yet another example, the user input component 616 is the same as the user input component 316, the display 618 is the same as the display 318, and the wired input/output component 620 is the same as the wired input/output component 320.

In one embodiment, the user input component 616 (e.g., the button) is configured to allow a user to change the state of the device 610. For example, the user, by pressing the button 616, changes the device 610 from the "display on" state to the "display off" state, or from the "display off" state to the "display on" state. In another example, under the "display on" state, the display 618 is turned on, and under the "display off" state, the display 618 is turned off (e.g., in order to save power when the user does not need to read the data). In yet another example, the user, by pressing the button 616 multiple times, cycles through a series of states of the device 610 that includes the "display off" state and one or more "display on" states. In yet another example, the one or more "display on" states include a state for displaying the historical temperature range, a state for displaying the highest measured temperature, its duration, and its date, a state for displaying the second highest measured temperature, its duration, and its date, a state for displaying the lowest temperature, its duration, and its date, and/or a state for displaying the historical relative humidity range.

In another embodiment, the display 618 is configured to display to the user data that are stored in the device 610. For example, the display 618 is configured to display one or more measured temperatures of the ambient air that is close to but outside the container 612, one or more measured temperatures of the container 612, and/or one or more temperatures of the liquid that is inside the container 612. In another example, the one or more temperatures of the liquid is determined by the device 610 (e.g., by a microcontroller as part of the device 610) based on the one or more measured temperatures of the ambient air and/or the one or more measured temperatures of the container 612. In yet another example, the display 618 is configured to display one or more measured relative humidity data of the ambient air that is close to but outside the container 612.

In yet another embodiment, the wired input/output component 620 (e.g., the connector) is configured to allow a user to charge and/or recharge the device 610, and/or to transfer data from and/or to the device 610. For example, the data are transferred between the device 610 and a smartphone, or between the device 610 and a computer. In another example, the data are stored in the device 610 before the data are transferred out of the device 610 or after the data are transferred into the device 610. In yet another example, the connector 620 is a USB connection port or another type of wired connection port that allows electric charging and/or recharging and/or allows data transfer. In yet another example, the device 610 is configured to alert a user that electric charging or recharging is needed by providing warning sound, by providing wired and/or wireless electronic signal, and/or by providing visual display (e.g., on the display 618). In yet another embodiment, the housing 614 is tamper resistant so that the data stored in the device 610 cannot be improperly altered and/or the device 610 cannot be improperly replaced by another device that stores counterfeit data.

As discussed above and further emphasized here, FIG. 6 is merely an example, which should not unduly limit the scope of the claims. One of ordinary skill in the art would recognize many variations, alternatives, and modifications. For example, the wired input/output component 620 (e.g., the connector) is removed. In one embodiment, the device 610 is configured to provide wireless data connection (e.g., by Bluetooth, Induction Wireless, WiFi, RFID, and/or cellular wireless connection), and/or provide wireless electric charging and recharging (e.g. by near-field RF). In another embodiment, the device 610 is configured to charge and recharge itself by harvesting energy from the ambient environment (e.g., from vibration and/or from stray EMF). In another example, the user input component 616 (e.g., the button) is removed. In one embodiment, the display 618 is a touch screen. In another embodiment, the user uses the touch screen (e.g., use a virtual button displayed on the display 618) to change the state of the device 610.

FIG. 7 is a simplified diagram showing a side view of a device for measuring and processing one or more conditions of a container according to one embodiment of the present invention, and FIG. 8 is a simplified diagram showing a top view of the device for measuring and processing the one or more conditions of the container according to one embodiment of the present invention. These diagrams are merely examples, which should not unduly limit the scope of the claims. One of ordinary skill in the art would recognize many variations, alternatives, and modifications.

As shown in FIGS. 7 and 8, the device 710 (e.g., a powered device) is configured to measure, record, and display one or more ambient conditions (e.g., ambient temperature and/or ambient relative humidity) of the container 712. For example, the container 712 is a liquid-containing bottle. In another example, the device 710 is enclosed in a housing 714 that is embedded, partially or completely, in the neck of the container 712 (e.g., in the neck of a liquid-containing bottle). In yet another example, the device 710 includes a user input component 716 (e.g., a button), a display 718, and a wired input/output component 720 (e.g., a connector). In yet another example, the user input component 716, the display 718, and the wired input/output component 720 are housed on the top of the device 710. In yet another example, the device 710 is the same as the device 300 with the humidity sensor 334 being exposed to the ambient air of the container 712. In yet another example, the user input component 716 is the same as the user input component 316, the display 718 is the same as the display 318, and the wired input/output component 720 is the same as the wired input/output component 320.

In one embodiment, the user input component 716 (e.g., the button) is configured to allow a user to change the state of the device 710. For example, the user, by pressing the button 716, changes the device 710 from the "display on" state to the "display off" state, or from the "display off" state to the "display on" state. In another example, under the "display on" state, the display 718 is turned on, and under the "display off" state, the display 718 is turned off (e.g., in order to save power when the user does not need to read the data). In yet another example, the user, by pressing the button 716 multiple times, cycles through a series of states of the device 710 that includes the "display off" state and one or more "display on" states. In yet another example, the one or more "display on" states include a state for displaying the historical temperature range, a state for displaying the highest measured temperature, its duration, and its date, a state for displaying the second highest measured temperature, its duration, and its date, a state for displaying the lowest temperature, its duration, and its date, and/or a state for displaying the historical relative humidity range.

In another embodiment, the display 718 is configured to display to the user data that are stored in the device 710. For example, the display 718 is configured to display one or more measured temperatures of the ambient air that is close to but outside the container 712, one or more measured temperatures of the container 712, and/or one or more temperatures of the liquid that is inside the container 712. In another example, the one or more temperatures of the liquid is determined by the device 710 (e.g., by a microcontroller as part of the device 710) based on the one or more measured temperatures of the ambient air and/or the one or more measured temperatures of the container 712. In yet another example, the display 718 is configured to display one or more measured relative humidity data of the ambient air that is close to but outside the container 712. In yet another example, the display 718 is configured to display the moisture content of a semi-permeable seal of the container 712 (e.g., a cork of a wine bottle), where the moisture content is measured by the device 710.

In yet another embodiment, the wired input/output component 720 (e.g., the connector) is configured to allow a user to charge and/or recharge the device 710, and/or to transfer data from and/or to the device 710. For example, the data are transferred between the device 710 and a smartphone, or between the device 710 and a computer. In another example, the data are stored in the device 710 before the data are transferred out of the device 710 or after the data are transferred into the device 710. In yet another example, the connector 720 is a USB connection port or another type of wired connection port that allows electric charging and/or recharging and/or allows data transfer. In yet another example, the device 710 is configured to alert a user that electric charging or recharging is needed by providing warning sound, by providing wired and/or wireless electronic signal, and/or by providing visual display (e.g., on the display 718). In yet another embodiment, the housing 714 is tamper resistant so that the data stored in the device 710 cannot be improperly altered and/or the device 710 cannot be improperly replaced by another device that stores counterfeit data.

As discussed above and further emphasized here, FIGS. 7 and 8 are merely examples, which should not unduly limit the scope of the claims. One of ordinary skill in the art would recognize many variations, alternatives, and modifications. For example, the wired input/output component 720 (e.g., the connector) is removed. In one embodiment, the device 710 is configured to provide wireless data connection (e.g., by Bluetooth, Induction Wireless, WiFi, RFID, and/or cellular wireless connection), and/or provide wireless electric charging and recharging (e.g. by near-field RF). In another embodiment, the device 710 is configured to charge and recharge itself by harvesting energy from the ambient environment (e.g., from vibration and/or from stray EMF). In another example, the user input component 716 (e.g., the button) is removed. In one embodiment, the display 718 is a touch screen. In another embodiment, the user uses the touch screen (e.g., use a virtual button displayed on the display 718) to change the state of the device 710.

FIG. 9(A) is a simplified diagram showing a side view of a device for measuring and processing one or more conditions of a container according to one embodiment of the present invention, and FIG. 9(B) is a simplified diagram showing a cross-section view of part of the device for measuring and processing the one or more conditions of the container according to one embodiment of the present invention. These diagrams are merely examples, which should not unduly limit the scope of the claims. One of ordinary skill in the art would recognize many variations, alternatives, and modifications.

As shown in FIG. 9(B), the cross-section view is taken along the thickness of the wall of the container 912. As shown in FIGS. 9(A) and (B), the device 910 (e.g., a powered device) is configured to measure, record, and display one or more ambient conditions (e.g., ambient temperature and/or ambient relative humidity) of the container 912. For example, the container 912 is a liquid-containing bottle. In another example, the device 910 is enclosed in a housing 914 that is embedded, partially or completely, inside the material construction (e.g., wall) of the container 912 (e.g., inside the material construction, such as wall, of a liquid-containing bottle). In yet another example, the device 910 includes a user input component 916 (e.g., a button), a display 918, and a wired input/output component 920 (e.g., a connector). In yet another example, the user input component 916, the display 918, and the wired input/output component 920 are housed on the side of the device 910. In yet another example, the device 910 is the same as the device 300 with the humidity sensor 334 being exposed to the ambient air of the container 912. In yet another example, the user input component 916 is the same as the user input component 316, the display 918 is the same as the display 318, and the wired input/output component 920 is the same as the wired input/output component 320.

In one embodiment, the user input component 916 (e.g., the button) is configured to allow a user to change the state of the device 910. For example, the user, by pressing the button 916, changes the device 910 from the "display on" state to the "display off" state, or from the "display off" state to the "display on" state. In another example, under the "display on" state, the display 918 is turned on, and under the "display off" state, the display 918 is turned off (e.g., in order to save power when the user does not need to read the data). In yet another example, the user, by pressing the button 916 multiple times, cycles through a series of states of the device 910 that includes the "display off" state and one or more "display on" states. In yet another example, the one or more "display on" states include a state for displaying the historical temperature range, a state for displaying the highest measured temperature, its duration, and its date, a state for displaying the second highest measured temperature, its duration, and its date, a state for displaying the lowest temperature, its duration, and its date, and/or a state for displaying the historical relative humidity range.

In another embodiment, the display 918 is configured to display to the user data that are stored in the device 910. For example, the display 918 is configured to display one or more measured temperatures of the ambient air that is close to but outside the container 912, one or more measured temperatures of the container 912, and/or one or more temperatures of the liquid that is inside the container 912. In another example, the one or more temperatures of the liquid is determined by the device 910 (e.g., by a microcontroller as part of the device 910) based on the one or more measured temperatures of the ambient air and/or the one or more measured temperatures of the container 912. In yet another example, the display 918 is configured to display one or more measured relative humidity data of the ambient air that is close to but outside the container 912.

In yet another embodiment, the wired input/output component 920 (e.g., the connector) is configured to allow a user to charge and/or recharge the device 910, and/or to transfer data from and/or to the device 910. For example, the data are transferred between the device 910 and a smartphone, or between the device 910 and a computer. In another example, the data are stored in the device 910 before the data are transferred out of the device 910 or after the data are transferred into the device 910. In yet another example, the connector 920 is a USB connection port or another type of wired connection port that allows electric charging and/or recharging and/or allows data transfer. In yet another example, the device 910 is configured to alert a user that electric charging or recharging is needed by providing warning sound, by providing wired and/or wireless electronic signal, and/or by providing visual display (e.g., on the display 918). In yet another embodiment, the housing 914 is tamper resistant so that the data stored in the device 910 cannot be improperly altered and/or the device 910 cannot be improperly replaced by another device that stores counterfeit data.

As discussed above and further emphasized here, FIGS. 9(A) and (B) are merely examples, which should not unduly limit the scope of the claims. One of ordinary skill in the art would recognize many variations, alternatives, and modifications. For example, the wired input/output component 920 (e.g., the connector) is removed. In one embodiment, the device 910 is configured to provide wireless data connection (e.g., by Bluetooth, Induction Wireless, WiFi, RFID, and/or cellular wireless connection), and/or provide wireless electric charging and recharging (e.g. by near-field RF). In another embodiment, the device 910 is configured to charge and recharge itself by harvesting energy from the ambient environment (e.g., from vibration and/or from stray EMF). In another example, the user input component 916 (e.g., the button) is removed. In one embodiment, the display 918 is a touch screen. In another embodiment, the user uses the touch screen (e.g., use a virtual button displayed on the display 918) to change the state of the device 910.

According to another embodiment, a device for measuring and processing one or more conditions of a container includes one or more microcontrollers, one or more temperature sensors, and one or more humidity sensors. The one or more temperature sensors are configured to measure one or more temperatures of a container, inside the container, or outside the container, generate one or more temperature signals associated with one or more temperature data representing the measured one or more temperatures, and output the one or more temperature signals to the one or more microcontrollers. The one or more humidity sensors are configured to measure one or more humidity levels outside the container, generate one or more humidity signals associated with one or more humidity data representing the measured one or more humidity levels, and output the one or more humidity signals to the one or more microcontrollers. Additionally, the device includes one or more memories coupled to the one or more microcontrollers, and a housing configured to enclose at least the one or more microcontrollers and the one or more memories. The one or more microcontrollers are configured to receive the one or more temperature signals and the one or more humidity signals, process information associated with the one or more temperature signals and the one or more humidity signals, and store the one or more temperature data and the one or more humidity data to the one or more memories coupled to the one or more microcontrollers. The housing is tamper resistant and configured to prevent one or more users from altering the one or more temperature data and the one or more humidity data. For example, the device is implemented according to at least FIG. 1, FIG. 2, FIG. 3, FIG. 4, FIG. 5, FIG. 6, FIG. 7, FIG. 8, FIG. 9(A), and/or FIG. 9(B).

In another example, the device further includes one or more timing devices coupled to the one or more microcontrollers and configured to provide one or more date and time data for the one or more temperature data and the one or more humidity data. In yet another example, the one or more timing devices are one or more chronometers. In yet another example, the one or more microcontrollers are further configured to match the one or more date and time data with the one or more temperature data and the one or more humidity data respectively.

In yet another example, the device further includes one or more user input components configured to allow the one or more users to change the device from a first state to a second state, one or more displays configured to display at least some of the one or more temperature data and the one or more humidity data stored in the one or more memories, and one or more input/output components configured to transfer at least some of the one or more temperature data and the one or more humidity data out of the device. In yet another example, under the first state, the one or more displays are configured to show a historical temperature range using the one or more temperature data, and under the second state, the one or more displays are configured to show a historical relative humidity range using the one or more humidity data. In yet another example, the one or more input/output components include one or more wired input/output connectors. In yet another example, the one or more input/output components include one or more wireless transceivers. In yet another example, the device further includes one or more batteries coupled to the one or more microcontrollers and provide electric power, and the one or more input/output components are further configured to charge and recharge the one or more batteries using one or more external power sources.

In yet another example, the one or more microcontrollers are further configured to determine one or more additional data based on at least information associated with at least some of the one or more temperature data and the one or more humidity data, and store the determined one or more additional data to the one or more memories. In yet another example, the device further includes one or more optodes configured to measure one or more concentrations of one or more materials within a liquid content of the container. In yet another example, the device further includes one or more optical sensors configured to detect one or more optical signals to determine whether the container was emptied at any point in time. In yet another example, the device further includes one or more capacitive sensors configured to determine presence or absence of one or more materials within the container. In yet another example, the device further includes one or more GPS devices configured to detect one or more GPS signals to determine one or more positions of the container.

In yet another example, the housing is affixed to the bottom of the container (e.g., as shown in FIG. 1, FIG. 2, and/or FIG. 3). In yet another example, the housing is affixed around the exterior of the container (e.g., as shown in FIG. 3 and/or FIG. 4). In yet another example, the housing is affixed around the neck of the container (e.g., as shown in FIG. 3 and/or FIG. 5). In yet another example, the housing is affixed to the side of the container (e.g., as shown in FIG. 3 and/or FIG. 6). In yet another example, the housing is embedded in the neck of the container (e.g., as shown in FIG. 3, FIG. 7, and/or FIG. 8). In yet another example, the housing is embedded inside a wall of the container (e.g., as shown in FIG. 3, FIG. 9(A), and/or FIG. 9(B)).

In yet another example, the device further includes one or more accelerometers configured to detect one or more accelerations of the container, generate one or more acceleration signals associated with one or more acceleration data representing the measured one or more accelerations, and output the one or more acceleration signals to the one or more microcontrollers. The one or more microcontrollers are further configured to receive the one or more acceleration signals, process information associated with the one or more acceleration signals, and store the one or more acceleration data to the one or more memories coupled to the one or more microcontrollers. The housing is further configured to prevent the one or more users from altering the one or more acceleration data.

According to yet another embodiment, a device for measuring and processing one or more conditions of a container includes one or more microcontrollers, one or more temperature sensors, and one or more humidity sensors. The one or more temperature sensors are configured to measure one or more temperatures of a container, inside the container, or outside the container, generate one or more temperature signals associated with one or more temperature data representing the measured one or more temperatures, and output the one or more temperature signals to the one or more microcontrollers. The one or more humidity sensors are configured to measure one or more humidity levels outside the container, generate one or more humidity signals associated with one or more humidity data representing the measured one or more humidity levels, and output the one or more humidity signals to the one or more microcontrollers. Additionally, the device includes one or more memories coupled to the one or more microcontrollers, a housing configured to enclose at least the one or more microcontrollers and the one or more memories, and one or more displays coupled to the one or more microcontrollers. The one or more microcontrollers are configured to receive the one or more temperature signals and the one or more humidity signals, process information associated with the one or more temperature signals and the one or more humidity signals, determine one or more additional data based on at least information associated with the one or more temperature data or the one or more humidity data, and store the one or more temperature data, the one or more humidity data, and the determined one or more additional data to the one or more memories. The one or more displays are configured to display at least some of the determined one or more additional data stored in the one or more memories, and the housing is tamper resistant and configured to prevent one or more users from altering the one or more additional data. For example, the device is implemented according to at least FIG. 1, FIG. 2, FIG. 3, FIG. 4, FIG. 5, FIG. 6, FIG. 7, FIG. 8, FIG. 9(A), and/or FIG. 9(B).

In another example, the determined one or more additional data represent one or more temperatures of a liquid inside the container. In yet another example, the device further includes one or more accelerometers configured to detect one or more accelerations of the container, generate one or more acceleration signals associated with one or more acceleration data representing the measured one or more accelerations, and output the one or more acceleration signals to the one or more microcontrollers. The one or more microcontrollers are further configured to receive the one or more acceleration signals, process information associated with the one or more acceleration signals, determine the one or more additional data based on at least information associated with at least some of the one or more temperature data, the one or more humidity data, and the one or more acceleration data, and store the one or more acceleration data to the one or more memories. In yet another example, the determined one or more additional data include one or more rate-of-change data representing one or more rates of changes for the one or more temperature data, and the one or more displays are further configured to display at least some of the one or more rate-of-change data stored in the one or more memories. In yet another example, the one or more microcontrollers are further configured to determine the one or more additional data based on at least information associated with the one or more temperature data and the one or more humidity data.

According to yet another embodiment, a device for measuring and processing one or more conditions of a container includes one or more microcontrollers, one or more optodes, and one or more timing devices. The one or more optodes are configured to measure one or more concentrations of one or more materials within a gaseous content or a liquid content of a container, generate one or more concentration signals associated with one or more concentration data representing the measured one or more concentrations, and output the one or more concentration signals to the one or more microcontrollers. The one or more timing devices are coupled to the one or more microcontrollers and configured to provide one or more date and time data for the one or more concentration data. Additionally, the device includes one or more memories coupled to the one or more microcontrollers, and a housing configured to enclose at least the one or more microcontrollers and the one or more memories. The one or more microcontrollers are configured to receive the one or more concentration data and the one or more date and time data, process information associated with the one or more concentration data and the one or more date and time data, match the one or more date and time data with the one or more concentration data respectively, and store the one or more concentration data and the one or more date and time data to the one or more memories. For example, the device is implemented according to at least FIG. 1, FIG. 2, FIG. 3, FIG. 4, FIG. 5, FIG. 6, FIG. 7, FIG. 8, FIG. 9(A), and/or FIG. 9(B).

In another example, the one or more optodes are further configured to measure one or more oxygen concentrations in the air inside the container. In yet another example, the one or more optodes are further configured to measure one or more oxygen concentrations in a wine inside the container. In yet another example, the device further includes one or more displays configured to display at least some of the one or more concentration data and the matched one or more date and time data.

According to yet another embodiment, a method for measuring and processing one or more conditions of a container includes measuring one or more temperatures of a container, inside the container, or outside the container, generating one or more temperature signals associated with one or more temperature data representing the measured one or more temperatures, outputting the one or more temperature signals, measuring one or more humidity levels outside the container, generating one or more humidity signals associated with one or more humidity data representing the measured one or more humidity levels, and outputting the one or more humidity signals. Additionally, the method includes receiving the one or more temperature signals and the one or more humidity signals, processing information associated with the one or more temperature signals and the one or more humidity signals, storing the one or more temperature data and the one or more humidity data, and preventing one or more users from altering the one or more temperature data and the one or more humidity data. For example, the method is implemented according to at least FIG. 1, FIG. 2, FIG. 3, FIG. 4, FIG. 5, FIG. 6, FIG. 7, FIG. 8, FIG. 9(A), and/or FIG. 9(B).

According to yet another embodiment, a method for measuring and processing one or more conditions of a container includes measuring one or more temperatures of a container, inside the container, or outside the container, generating one or more temperature signals associated with one or more temperature data representing the measured one or more temperatures, outputting the one or more temperature signals, measuring one or more humidity levels outside the container, generating one or more humidity signals associated with one or more humidity data representing the measured one or more humidity levels, and outputting the one or more humidity signals to the one or more microcontrollers. Additionally, the method includes receiving the one or more temperature signals and the one or more humidity signals, processing information associated with the one or more temperature signals and the one or more humidity signals, determining one or more additional data based on at least information associated with the one or more temperature data or the one or more humidity data, storing the one or more temperature data, the one or more humidity data, and the determined one or more additional data, displaying at least some of the determined one or more additional data stored in the one or more memories, and preventing one or more users from altering the one or more additional data. For example, the method is implemented according to at least FIG. 1, FIG. 2, FIG. 3, FIG. 4, FIG. 5, FIG. 6, FIG. 7, FIG. 8, FIG. 9(A), and/or FIG. 9(B). In another example, the determining one or more additional data based on at least information associated with the one or more temperature data or the one or more humidity data includes determining the one or more additional data based on at least information associated with the one or more temperature data and the one or more humidity data.

According to yet another embodiment, a method for measuring and processing one or more conditions of a container includes measuring one or more concentrations of one or more materials within a gaseous content or a liquid content of a container, generating one or more concentration signals associated with one or more concentration data representing the measured one or more concentrations, outputting the one or more concentration signals, providing one or more date and time data for the one or more concentration data, receiving the one or more concentration data and the one or more date and time data, processing information associated with the one or more concentration data and the one or more date and time data, matching the one or more date and time data with the one or more concentration data respectively, and storing the one or more concentration data and the one or more date and time data to the one or more memories. For example, the method is implemented according to at least FIG. 1, FIG. 2, FIG. 3, FIG. 4, FIG. 5, FIG. 6, FIG. 7, FIG. 8, FIG. 9(A), and/or FIG. 9(B).

Certain embodiments of the present invention allow a person to know the historical ambient and handling conditions (e.g., the thermal and/or humidity history) which a container (e.g. a bottle of wine, a vial of medicine) experienced throughout its existence after the content was added and the container was closed and/or sealed. For example, various measurements are performed for the ambient temperature over time, the relative humidity over time, any experience of physical shock over time, the geographic coordinates over time, and/or the dissolved oxygen concentration within the liquid content (e.g., wine) of the container over time. In another example, various measurements are performed to determine whether the container was emptied at any point in time.

Some embodiments of the present invention provide a device (e.g., an automatic, electronic, and digital powered device) that is capable of various types of measurements (e.g., temperature measurement and/or relative humidity measurement) for containers (e.g., liquid-containing bottles). For example, the device is attached to or embedded in a liquid-containing bottle, and measures, records, and displays at least the ambient temperature and/or the relative humidity. In another example, the intimate proximity of the device to the bottle (e.g., physical contact of the device to the bottle for an extended period of time) improves measurement accuracy and the small form allows the user to easily transport the bottle and the device as needed.

Certain embodiments of the present invention provide a device to collect data for each individual container into which the device is incorporated and to record the data to the memory of the device such that the data can be retrieved at any time but not tampered with in any way so as to falsify the data. For example, the data collection, recording, and security mechanisms provide the users (e.g., the consumers), prior to opening or even purchasing the container and its content, with confidence in the recorded history of the conditions experienced by the container. In another example, the recorded history of the conditions may indicate the quality and/or efficacy of the content of the container has been adversely affected.

Although specific embodiments of the present invention have been described, it will be understood by those of skill in the art that there are other embodiments that are equivalent to the described embodiments. For example, various embodiments and/or examples of the present invention can be combined. Accordingly, it is to be understood that the invention is not to be limited by the specific illustrated embodiments, but only by the scope of the appended claims.

What is claimed is:

1. A device for measuring and processing one or more conditions of a container, the device comprising:
one or more microcontrollers;
one or more temperature sensors configured to measure one or more temperatures inside the container, generate one or more temperature signals associated with one or more temperature data representing the measured one or more temperatures inside the container, and output the one or more temperature signals to the one or more microcontrollers;
one or more humidity sensors configured to measure one or more humidity levels outside the container, generate one or more humidity signals associated with one or more humidity data representing the measured one or more humidity levels, and output the one or more humidity signals to the one or more microcontrollers;
one or more optodes configured to measure one or more concentrations of one or more first materials within a content of the container and generate one or more optode data;
one or more optical sensors configured to detect one or more optical signals and generate one or more optical data to determine whether the container was emptied at any point in time;
one or more capacitive sensors configured to generate one or more capacitive data to determine presence or absence of one or more second materials within the container;
one or more GPS devices configured to detect one or more GPS signals and generate one or more location data to determine one or more positions of the container;
one or more memories coupled to the one or more microcontrollers;
a housing configured to enclose at least the one or more microcontrollers and the one or more memories, the housing being embedded in a neck of the container; and
one or more displays coupled to the one or more microcontrollers;
wherein the one or more microcontrollers are configured to store the one or more temperature data, the one or more humidity data, the one or more optode data; the one or more optical date, the one or more capacitive data, and the one or more location data to the one or more memories coupled to the one or more microcontrollers;
wherein the one or more microcontrollers are further configured to:
determine one or more rate-of-change data representing one or more rates of changes for the one or more temperature data; and
store the determined one or more rate-of-change data to the one or more memories;
wherein:
the one or more displays are configured to display at least some of the one or more rate-of-change data stored in the one or more memories; and
the housing is tamper resistant and configured to prevent one or more users from altering the one or more temperature data, the one or more humidity data, and the one or more rate-of-change data;
wherein the one or more microcontrollers are further configured to:
process information associated with the one or more location data and the one or more capacitive data;
determine whether the content of the container has been re-routed to an unapproved site and removed from the container based on at least information associated with the one or more location data and the one or more capacitive data;
wherein the one or more microcontrollers are further configured to:
process information associated with the one or more temperature data, the one or more humidity data, and the one or more optode data;
determine an overall quality of the content as a function of storage conditions over time; and
indicate to a user an overall score and a specific timeframe for which the content of the container is best consumed.

2. The device of claim 1, and further comprising one or more timing devices coupled to the one or more microcontrollers and configured to provide one or more date and time data for the one or more temperature data and the one or more humidity data.

3. The device of claim 2 wherein the one or more timing devices are one or more chronometers.

4. The device of claim 2 wherein the one or more microcontrollers are further configured to match the one or more date and time data with the one or more temperature data and the one or more humidity data respectively.

5. The device of claim 1, and further comprising:
one or more user input components configured to allow the one or more users to change the device from a first state to a second state;
one or more displays configured to display at least some data stored in the one or more memories; and
one or more input/output components configured to transfer at least some data out of the device.

6. The device of claim 5 wherein:
under the first state, the one or more displays are configured to show a first historical range; and
under the second state, the one or more displays are configured to show a second historical range.

7. The device of claim 5 wherein the one or more input/output components include one or more wired input/output connectors.

8. The device of claim 5 wherein the one or more input/output components include one or more wireless transceivers.

9. The device of claim 5, and further comprising:
one or more batteries coupled to the one or more microcontrollers and provide electric power;
wherein the one or more input/output components are further configured to charge and recharge the one or more batteries using one or more external power sources.

10. The device of claim 1, and further comprising:
one or more accelerometers configured to detect one or more accelerations of the container, generate one or more acceleration signals associated with one or more acceleration data representing the measured one or more accelerations, and output the one or more acceleration signals to the one or more microcontrollers;
wherein the one or more microcontrollers are further configured to:
receive the one or more acceleration signals;

process information associated with the one or more acceleration signals; and store the one or more acceleration data to the one or more memories coupled to the one or more microcontrollers;

wherein the housing is further configured to prevent the one or more users from altering the one or more acceleration data.

\* \* \* \* \*